US005227295A

United States Patent [19]

Baker

[11] Patent Number: 5,227,295

[45] Date of Patent: Jul. 13, 1993

[54] PROCESS FOR ISOLATING A83543 AND ITS COMPONENTS

[75] Inventor: Patrick J. Baker, Greenwood, Ind.

[73] Assignee: DowElanco, Indianapolis, Ind.

[21] Appl. No.: 790,283

[22] Filed: Nov. 8, 1991

[51] Int. Cl.$^5$ ....................... C12P 19/60; C12P 19/62; C12R 1/01

[52] U.S. Cl. ....................................... 435/76; 435/75; 435/803; 435/822; 536/7.1; 536/7.5

[58] Field of Search .................... 536/7.5, 7.1; 435/75, 435/76, 803, 822

[56] References Cited

U.S. PATENT DOCUMENTS

| | | | |
|---|---|---|---|
| 4,148,883 | 4/1979 | Celmer et al. . | |
| 4,206,206 | 6/1980 | Mori et al. . | |
| 4,224,314 | 9/1980 | Celmer et al. . | |
| 4,261,511 | 2/1981 | Whaley et al. . | |
| 4,293,651 | 10/1981 | Whaley et al. . | |
| 4,321,329 | 3/1982 | Whaley et al. . | |
| 4,448,970 | 5/1984 | Magerlein . | |
| 4,501,752 | 2/1985 | Yokoi et al. . | |
| 4,508,647 | 4/1985 | Hatori et al. | 435/119 |
| 4,515,942 | 5/1985 | Iwasaki et al. . | |
| 4,530,835 | 7/1985 | Bunge et al. | 435/169 |
| 4,560,509 | 12/1985 | Johnson et al. | 435/119 |
| 4,568,740 | 2/1986 | Oppici et al. | 536/7.5 |
| 5,003,056 | 3/1991 | Nishikiori et al. | 435/76 |
| 5,028,536 | 7/1991 | Golik et al. | 435/101 |

FOREIGN PATENT DOCUMENTS

| | | |
|---|---|---|
| 375316 | 6/1990 | European Pat. Off. . |
| 46-028833 | 8/1971 | Japan . |
| 48-039922 | 11/1973 | Japan . |
| 55-000310 | 1/1980 | Japan . |
| 59-151896 | 8/1984 | Japan . |
| 59-170092 | 9/1984 | Japan . |
| 60-160888 | 8/1985 | Japan . |
| 60-053597 | 11/1985 | Japan . |
| 62-226925 | 10/1987 | Japan . |
| 63-045280 | 2/1988 | Japan . |

OTHER PUBLICATIONS

Biosis Abstract 90:127301 Mertz et al. "Int. J. Syst. Bact" 40(1) 1990 34–39.

ATCC Catalogue "Bacteria & Bacteriophages" 17th Ed 1989 Editor Gherna et al. p. 190.

Catalogue of bacteria and phages, ATCC, 7th Ed., 1989.

Umezawa, Institute of Microbial Chemistry, Tokyo, Index of Antibi. from Actinomycetes, vol. I.

Umezawa, Supplement to Index of Antibiotics from Actinomycetes.

Derwent Abstract 85-245719/40, SSSE Feb. 1, 1984.

Derwent Abstract 54333S-BCD, Fuji, Feb. 17, 1969.

Derwent Abstract 80-11667C/07.

Derwent Abstract 84-278337/45, SSSE Mar. 16, 1983.

Derwent Abstract 84-252941/41, SSSE Feb. 16, 1983.

Derwent Abstract 92:144960k.

(List continued on next page.)

*Primary Examiner*—Herbert J. Lilling

*Attorney, Agent, or Firm*—Donald R. Stuart; Thomas D. Zindrick; Kenneth L. Loertscher

[57] ABSTRACT

An improved process for isolating A83543 factors from fermentation broth in which they are produced which comprises:

a) adding an approximately equal volume of a water miscible, polar organic solvent to the fermentation broth, including the biomass thereof;

b) separating the liquid phase of the resulting mixture from the biomass;

c) adjusting the pH of the separated liquid phase to between about 7 and 13;

d) applying the separated liquid phase directly to a column of nonfunctional, macroreticular polymer;

e) eluting the A83543 components from the column with an aqueous solution of water miscible, polar organic solvent; and f) collecting the fractions containing A83543 components.

18 Claims, No Drawings

OTHER PUBLICATIONS

Derwent Abstract 11667c/07, KAKE May 31, 1978.
Derwent Abstract 92:211459u.
Derwent Abstract 88-095030/14, SSSE 1986.
Aizawa et al. (1979), J. Antibiot., 32:193.
Ito et al. (1972), Tetrahedron Letters, 11, 81, 1185, 2557.
Schulman and Ruby (1987), Antimicrobial Agents and Chemotherapy, 31(6):964-965.
Schulman et al. (1985), The Journal of Antibiotics, 1494-1498.
Ito and Hirata (1972), Tetrahedron Letters, 12:1185-1188.
Kirst et al., Tetrahedron Leters (1991), 32(37):4839-4842.
Whaley et al., Tetrahedron Ltrs., (1980), 21:3659.
Kreuzman et al., J. Biological Chemistry (1988), 263(30):15626-15633.
Snyder, et al., J. Am. Chem. Soc. (1984) 106:787.
Celmer et al., J. Chem. Soc. (1980) 102:4203.
Aizawa et al. (1979), The Journal of Antibiotics, 22(3):193-196.
Ikeda et al., (1985), J. Antibiotic, 38:436.
Jomon et al., (1972), The Journal of Antibiotics, 25(5):271-280.
Dybas and Babu (1988), Brighton Crop Protection Conference, 57-64.
Borchardt et al. (1979), Biochem. & Biophys. Res. Comm., 89(3):919-924.
Vedel et al., (1978), Biochem. & Biophys. Res. Comm., 85(1):371-376.
Pickett, J. A., (1988), Chemistry in Britain, 137-142.
Omura, (1984), Macrolide Antibiotics, Chapter 13.
Fuller (1978), Biochemical Pharmacology, 27:1981-1983.
Jackson et al. (1988), Abstracts of the 1988 ICAAC, 26026.
Umezawa (1980), The Journal of Antibiotics, 33(3):15-26.
Umezawa, Index of Antibiotics from Actinomycetes, vol. 2.
Omura and Tannaka (1984), Macrolide Antibiotics, Chapter 1.

PROCESS FOR ISOLATING A83543 AND ITS COMPONENTS

FIELD OF THE INVENTION

This invention provides an improved process for isolating A83543 and its separate components from the fermentation broth in which it is produced.

BACKGROUND OF THE INVENTION

Fermentation product A83543, a family of related factors produced by *Saccharopolyspora spinosa*, was recently discovered and was shown to exhibit excellent insecticidal activity. In European Patent Publication No. 0 375 316 fermentation product A83543 was shown to comprise individual components A83543A, A83543B, A83543C, A83543D, A83543E, A83543F, A83543G, A83543H, and A83543J. The general structure of the A83543 factors consists of a 5,6,5-tricyclic ring system fused to a 12-membered macrocyclic lactone, a neutral sugar, and an amino sugar. Kirst et al., *Tetrahedron Letters,* 32, 4839 (1991).

The U.S. patent application of Jon S. Mynderse et al. on "New A83543 Compounds and Processes for Production Thereof" (U.S. application Ser. No. 07/790,287) the same date as this application is hereby incorporated herein by reference. That application discloses factors A83543L, A83543M, and A83543N.

The following table identifies by structure these known A83543 components.

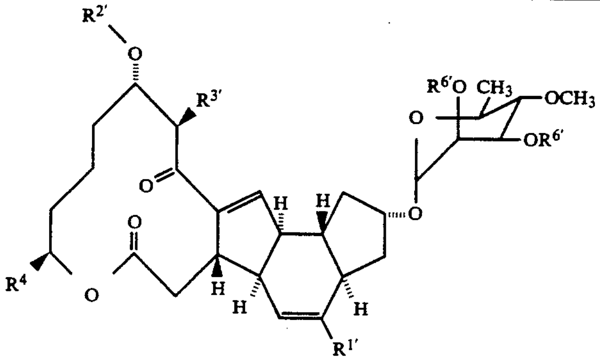

| Factor | $R^3$ | $R^1$ | R | $R^4$ | $R^5$ | $R^6$ |
|---|---|---|---|---|---|---|
| A83543A | H | $CH_3$ | 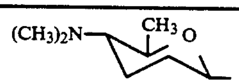 | $C_2H_5$ | $CH_3$ | $CH_3$ |
| A83543B | H | $CH_3$ | 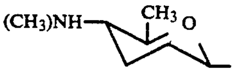 | $C_2H_5$ | $CH_3$ | $CH_3$ |
| A83543C | H | $CH_3$ | 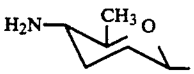 | $C_2H_5$ | $CH_3$ | $CH_3$ |
| A83543D | $CH_3$ | $CH_3$ | 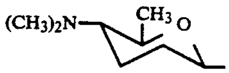 | $C_2H_5$ | $CH_3$ | $CH_3$ |
| A83543E | H | $CH_3$ | 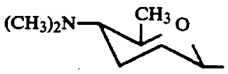 | $CH_3$ | $CH_3$ | $CH_3$ |
| A83543F | H | H | 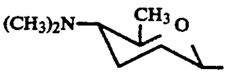 | $C_2H_5$ | $CH_3$ | $CH_3$ |
| A83543G | H | $CH_3$ | 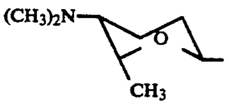 | $C_2H_5$ | $CH_3$ | $CH_3$ |
| A83543H | H | $CH_3$ | 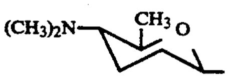 | $C_2H_5$ | H | $CH_3$ |
| A83543J | H | $CH_3$ | 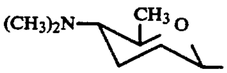 | $C_2H_5$ | $CH_3$ | H |
| A83543L | $CH_3$ | $CH_3$ | 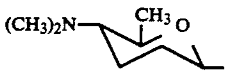 | $C_2H_5$ | $CH_3$ | H |

-continued

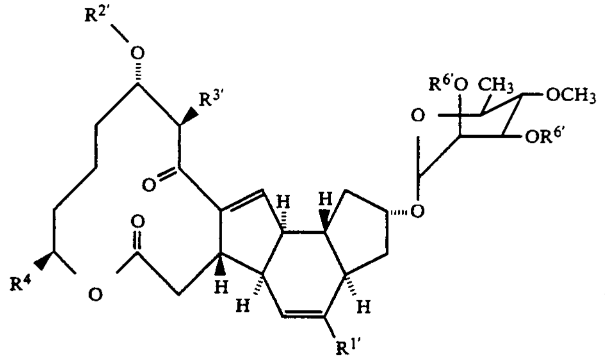

| Factor | $R^3$ | $R^1$ | R | $R^4$ | $R^5$ | $R^6$ |
|---|---|---|---|---|---|---|
| A83543M | H | $CH_3$ | 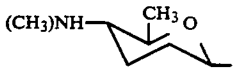 | $C_2H_5$ | $CH_3$ | H |
| A83543N | $CH_3$ | $CH_3$ | 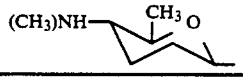 | $C_2H_5$ | $CH_3$ | H |

A83543 and each of the components are useful for the control of mites and insects, particularly Lepidoptera and Diptera species.

The term "A83543 component" means a compound selected from the group consisting of A83543A, A83543B, A83543C, A83543D, A83543E, A83543F, A83543G, A83543H, A83543J, A83543L, A83543M, and A83543N. If additional factors of the similar structure are subsequently discovered, it is contemplated that the isolation process provided by this invention will be applicable to them as well.

A83543 is produced by culturing an A83543-producing strain of *Saccharopolyspora spinosa* under submerged aerobic conditions by methods disclosed in the copending U.S. patent application of LaVerne D. Boeck et al., on "A83543A Compounds", U.S. application Ser. No. 07/773,754, filed Oct. 10, 1991 "A83543 Compounds," Ser. No; 07/429,441, filed Oct. 30, 1989, now abandoned and the above identified application of Jon S. Mynderse et al. on "New A83543 Compounds and Processes for Production Thereof" (U.S. application Ser. No. 07/790,287).

The term "A83543-producing strain of *Saccharopolyspora spinosa*" means a strain of *Saccharopolyspora spinosa* capable of producing recoverable amounts of at least one A83543 component. The following six A83543-producing *Saccharopolyspora spinosa* cultures, A83543.1, A83543.3, A83543.4, A83543.5, A83543.6, and A83543.7,have been deposited and made a part of the stock culture collection of the Midwest Area Regional Research Center, Agricultural Research Service, U.S. Department of Agriculture, from which they are available to the public under the following accession numbers:

| NRRL No. | Strain No. |
|---|---|
| 18395 | A83543.1 |
| 18537 | A83543.3 |
| 18538 | A83543.4 |
| 18539 | A83543.5 |
| 18719 | A83543.6 |
| 18720 | A83543.7 |

The characteristics of these cultures are described in detail in the above identified U.S. patent applications of LaVerne D. Boeck et al. and Jon W. Mynderse et al. Each of the strains A83543.3, A83543.4, A83543.5, A83543.6, and A83543.7 was derived from A83543.1 by means described in those patent applications.

As is the case with other organisms, the characteristics of the A83543-producing strains are subject to variation. Thus, mutants of these strains may be obtained by physical and chemical methods known in the art. For example, other strains may be obtained by treatment with chemicals such as N-methyl-N'-nitro-N-nitrosoguanidine. Natural and induced mutants derived directly or indirectly from A83543.1 which retain the characteristic of producing recoverable amounts of at least one A83543 component are applicable in the present invention.

The culture medium used to grow these *Saccharopolypora spinosa* cultures can be any one of a number of media. For economy in production, optimal yield, and ease of product isolation, certain culture media are preferred. For example, preferred carbon sources in large-scale fermentation are glucose and methyl oleate, although ribose, xylose, fructose, galactose, mannose, mannitol, maltose, soluble starch, potato dextrin, oils such as soybean oil and the like can also be used. Preferred nitrogen sources are cottonseed flour, peptonized milk and corn steep liquor, although fish meal, digested soybean meal, yeast extract, enzyme-hydrolyzed casein, beef extract, and the like can also be used. Among the nutrient inorganic salts which can be incorporated in the culture media are the customary soluble salts capable of yielding zinc, sodium, magnesium, calcium, ammonium, chloride, carbonate, sulfate, nitrate and like ions. Essential trace elements necessary for the growth and development of the organism should also be included in the culture medium. Such trace elements commonly occur as impurities in other substituents of the medium in amounts sufficient to meet the growth requirements of the organism.

Usually, if forming is a problem, small amounts (i.e., 0.2 ml/L) of an antifoam agent such as polypropylene glycol may be added to large-scale fermentation media.

In the case of the A83543-producing cultures, however, conventional defoamers inhibit A83543 production. Foaming is controlled by including soybean oil or PLURONIC L-101 (BASF, Parsippany, N.J.) in the medium (1-3%). Additional oil is added if foaming develops.

The A83543 components are produced by the A83543-producing organisms when grown at temperatures between about 24° and about 33° C. Optimum temperatures for production appear to be about 28°-30° C.

As is customary in submerged aerobic culture processes, sterile air is blown into the vessel from the bottom while the medium is stirred with conventional turbine impellors. In general, the aeration rate and agitation rate should be sufficient to maintain the level of dissolved oxygen at or above 60% of air saturation, preferably above 65%, with an internal vessel pressure of about 0.34 atmospheres.

Production of the A83543 components can be followed during the fermentation by testing extracts of the broth. A preferred method for following the production is analysis of the broth extracts by high performance liquid chromatography (HPLC). A suitable system for analysis is described in Example 1.

The A83543 components produced during fermentation of the A83543-producing organism occurs in both the mycelial mass (the biomass) and the broth. A83543 components are lipophilic. Separation of the lipophilic A83543 components from the broth has proved to be a significant problem, because it requires a simultaneous separation of the components from the substantial quantity of oil used to control foaming during the fermentation.

Prior to this invention, A83532 components were isolated by the method described in U.S. patent application of Patrick J. Baker on "A83543 Recovery Process," Ser. No. 07/451,394, filed Dec. 15, 1989. Although the process described in that patent application is a significant improvement over prior processes, there remained a need to improve the efficiency of the recovery operation.

SUMMARY OF THE INVENTION

This invention provides a process for isolating A83543 factors from fermentation broth in which they are produced which comprises:

a) adding an approximately equal volume of a water miscible, polar organic solvent to the fermentation broth, including the biomass thereof;

b) separating the liquid phase of the resulting mixture from the biomass;

c) adjusting the pH of the separated liquid phase to between about 7 and 13;

d) applying the separate liquid phase directly to a column of nonfunctional, macroreticular polymer;

e) eluting the A83543 components from the column with an aqueous solution of water miscible, polar organic solvent; and f) collecting the fractions containing A83543 components.

DETAILED DESCRIPTION OF THE INVENTION

As used herein the term "water miscible, polar organic solvent" encompasses mixtures of one or more water miscible, polar organic solvents, with or without water.

In step a) the whole fermentation broth may be used. Preferred "water miscible, polar organic solvents" are acetone and acetonitrile. The function of this step is to extract the A83543 components from the biomass. Other water miscible, polar organic solvents in which the components are readily soluble may also be used.

Step b) is preferably carried out by filtering the mixture produced in step a) through a ceramic filter. The filtrate produced by this step contains the oil that was added to the broth during fermentation to control foaming.

The pH adjustment called for in step c) assures that the A83543 components will be in the bas form. The base form is absorbed more strongly on the nonfunctional, macroreticular polymer. A preferred pH range is from 7 to 10. The value is not critical, provided the A83543 components are in the base form. Possible instability of the A83543 compounds becomes of increasing concern when the pH exceeds 10. The pH adjustment is conveniently made using sodium hydroxide, but the base used is not critical.

The preferred nonfunctional, macroreticular polymer for use in step d) is a nonfunctional polystyrene cross-linked with divinyl benzene polymer such as Diaion HP-20ss (Mitsubishi Chemical Industries, Co., Ltd., Japan).

Following step d) and prior to step e), the loaded column may optionally be washed with an aqueous solution of water miscible, polar organic solvent to displace the broth from the column. A preferred organic solvent is methanol/acetonitrile/water (1:1:2). The organic component of the solvent should not be so small as to cause a potential for precipitation of material in the column, nor so large as to cause A83543 components to be eluted at this stage. The solvent is preferably 30% to 70% aqueous, and more preferably above 50% aqueous. By removing the oily impurities in this step the purity of the A83543 components is significantly improved.

The water miscible, polar organic solvent used in step e) is preferably a 95:5 mixture of methanol/acetonitrile (1:1) containing 0.1% ammonium acetate to control pH (pH 8.1). Other polar organic solvents, such as acetone can also be used. Ammonium acetate is the preferred buffer, because it is volatile and easily removed from the A83543 components.

The fractions containing the A83543 components are combined, concentrated, and optionally lyophilized.

The advantages of this method over the previously used method are:

1) recovery of purified A83543 components can be achieved as part of this process, whereas the previous method provided no factor separation;

2) improved recovery of purified A83543 components by reducing the number of isolation steps; and 3) elimination of costly and time consuming distillation steps.

The invention is illustrated in further detail by the following detailed procedures, preparations, and examples. The examples are for purposes of illustration only, and are not to be construed as limiting the scope of the present invention. All parts and percentages are by weight unless specifically noted.

A83543 Assay Method

The following analytical high performance liquid chromatography (HPLC) method is useful for monitoring a fermentation for the production of A83543 components:

A sample of the whole broth is diluted with three volumes of acetonitrile to extract the factors from the mycelia. The resulting solution is then filtered through a 0.45 micron PTFE filter to remove particulate matter prior to injection into the HPLC assay system. A solution of purified A83543A at a concentration of 100 $\mu$g/ml in methanol is used as an external standard for the assay and peak areas of all A83543 components are related back to this calibration standard to determine concentrations of individual factors.

HPLC System:

Column Support: 4.6×100-mm column, ODS-AQ, 5$\mu$ spherical particles, 120Å pore (YMC, Inc., Morris Plains, N.J.)

Mobile Phase: $CH_3CN/MeOH/H_2O$ (40/40/20) containing 0.05% ammonium acetate

Flow Rate: 3 mL/min

Detection: UV at 250 nm

| Retention Times: | |
|---|---|
| A83543A | 9.1 min |
| A83543J | 5.7 min |
| A83543L | 7.3 min |
| A83543M | 2.6 min |
| A83543N | 3.3 min |

Preparation 1

Preparation of A83543J, A83543L, A83543M, and A83543N with Culture A83543.6

A. Shake-flask Fermentation

The culture *Saccharopolyspora spinosa* NRRL 18719, either as a lyophilized pellet or as a suspension maintained in liquid nitrogen, was used to inoculate a vegetative medium having the following composition:

| Vegetative Medium | |
|---|---|
| Ingredient | Amount (g) |
| Trypticase broth* | 30 |
| Yeast extract | 3 |
| $MgSO_4.7H_2O$ | 2 |
| Glucose | 5 |
| Maltose | 4 |
| Deionized water | q.s. 1 L |

Autoclave 30 min at 120° C.
*Baltimore Biological Laboratories, Cockeysville, MD Slants or plates can be prepared by adding 2.5% agar to the vegetative medium. The inoculated slant is incubated at 30° C. for about 10 to about 14 days. The mature slant culture is scraped with a sterile tool to loosen the spores and to remove and macerate the mycelial mat. About one-fourth of the loosened spores and culture growth thus obtained is used to inoculate 50 ml of a first-stage vegetative medium. Alternatively, the first-stage medium may be inoculated from a liquid nitrogen ampoule.

When culture is maintained in liquid nitrogen, ampoules are prepared by homogenizing a vegetative culture 48–72 hours incubation, 30° C.), diluting 1:1 (volume:volume) with a sterile suspending agent, and agent contains lactose (100 g), glycerol (200 ml), and deionized water (q.s. to 1 L).

A liquid nitrogen ampoule is used to inoculate 100 ml of vegetative medium in 500-ml Erlenmeyer flasks (or 50 ml of medium in 250-ml flasks). The cultures are incubated at 30° C. for 48 hours on a shaker orbiting in a two-inch (5.08 cm) circle at 260 rpm.

The incubated culture (10% v/v inoculum) is used to inoculate 50 ml or 100 ml, dependent on the size of the Erlenmeyer flask, of a production medium having the following composition:

| Production Medium | |
|---|---|
| Ingredient | Amount (g) |
| Glucose | 80 |
| Peptonized milk* | 20 |
| Cottonseed flour** | 30 |
| Corn steep liquor | 10 |
| $CaCO_3$ (tech. grade) | 5 |
| Methyl oleate | 30*** |
| Tap water | q.s. to 1 L |

pH adjusted to pH 7.0 with IN NaOH, sterilized 40 min. at 120° C.
*Peptonized Milk Nutrient, Sheffield Products, Norwich, NY 13815
**Proflo, Traders Protein, Memphis TN 38108
***The amount of methyl oleate was 30 ml The inoculated production medium is incubated in 250-ml or 500-ml Erlenmeyer flasks at 30° C. for 7 to 10 days on a shaker orbiting in a two-inch circle at 260 rpm.

B. Stirred Reactor Fermentation

In order to provide a larger volume of inoculum, 10 ml of incubated first stage medium, prepared as described in Section A, is used to inoculate 400 ml of a second-stage vegetative medium having the same composition as that of the first-stage medium. This second-stage vegetative medium is incubated in a 2-L wide-mouth Erlenmeyer flask for about 48 hours at 30° C. on a shaker orbiting in a two-inch circle at 260 rpm. Incubated second-stage vegetative medium (2 L) thus prepared is used to inoculate 80 to 115 liters of sterile production medium, prepared as described in Section A.

The inoculated production medium is allowed to ferment in a 165-L stirred bioreactor for 7 days to 10 days at a temperature of 30° C. The air-flow and agitator speed in the stirred vessel are computer controlled to maintain a dissolved oxygen level at or above 60% to about 80% of air saturation.

COMPARATIVE EXAMPLE

Isolation of A83543J, A83543L, A83543M, and A83543N

Fermentation broth (105 L), prepared as described in Preparation 1, was adjusted to pH 10 (initially pH 6.8) by adding 5N NaOH. The resulting mixture was filtered through a ceramic filter. The filtrate was discarded, a mixture of acetone and water (1:1, 50 L) was added to the mycelial solids, and the resulting mixture was filtered. A second mixture of acetone and water (1:1, 50 L) was added to the mycelial solids, and the pH of the resulting mixture was mixture was filtered, and a third mixture of acetone and water (1:1 50 L) was added to the mycelial solid. The resulting mixture was filtered and the acidic filtrates were combined. The combined filtrates were extracted with heptane (10 L). The phases were separated and the aqueous phase added to a second portion of heptane (10 L). The pH of the resulting mixture was adjusted to pH 10 with 5N NaOH. The resulting emulsion was diluted with 50 L of water. The phases were separated and the aqueous phase extracted with a third portion of heptane (10 L). The phases were separated and the second and third heptane extracts were combined and concentrated to a volume of about 4 liters. Upon standing, the concentrate separated into 3 phases: aqueous, emulsion, and organic. The organic phase was lyophilized to give 15.29 g of crude product.

The crude product was dissolved in methanol (500 mL), filtered, and concentrated to dryness in vacuo. The residue was dissolved in a second portion of methanol (20 ml) and applied to a column of LH-20 SEPHADEX (Pharmacia KB Biotechnology, Inc., Piscataway, N.J., 7.5 cm×46 cm), eluting with methanol and collecting 25 ml fractions. Using the HPLC system described in Example 1, the fractions were analyzed to determine which fractions contained the formula 2 compounds. Fractions 18–50 were combined and concentrated to dryness.

The residue was dissolved in a mixture of ethanol, acetonitrile, and water (5:5:1) and chromatographed in 1 ml portions on a preparative reverse-phase HPLC column (Rainin DYNAMAX060A, C18, 41.4 mm×300 mm, 8 μm particles, 60Å pore, Woburn, Mass.). The column was eluted with a mixture of methanol, acetonitrile and water (87.5:87.5:25) with ammonium acetate added to a final concentration of 0.1% (pH 7.6). The fractions were analyzed using an HPLC system, similar to that as described in Example 1, combining like fractions and concentrating to give three semi-pure concentratrates A, B, and C.

Semi-pure concentrate C was rechromatographed on the system described in the preceding paragraph, loading 200 mL on each of 10 runs. The fractions from each of the runs were combined and concentrated to give preparations C1 and C2. Preparation C2 was chromatographed a third time; however, water was used in place of the 0.1% ammonium acetate (desalting step). Fractions containing A83543L in at least 99.5% HPLC purity were combined and concentrated. The residue was crystallized from ethanol/water (1:1) to give 2.4 g of A83543L.

Preparation C1 and semi-pure concentrate B were combined and desalted as described in the preceding paragraph (12×200 mL runs); however, the desired compound was eluted with a mixture of methanol, acetonitrile, and water (11:11:3). The fractions containing A83543J in at least 99.5% HPLC purity were combined and concentrated. The residue was dissolved in hot t-butanol and lyophilized to give 4.3 g of A83543J.

Semi-pure concentrate A was chromatographed as described above, except the desired compounds were eluted with a mixture of methanol, acetonitrile, and water (37.5:37.5:25), with ammonium acetate added to final concentration of 0.1%. The fractions from each of the runs (4) were combined and concentrated to give preparations A1, A2, and A3.

Preparation A1 was chromatographed using the column described above; however, the column was eluted with a mixture of methanol, acetonitrile, and water (2:2:1). Fractions containing A83543M in at least 99.5% HPLC purity were combined and concentrated. The residue was dissolved in t-butanol and lyophilized to give 136 mg of A83543M.

Preparation A2 was chromatographed and processed as described in the preceding paragraph to give 71 mg of A83543N.

EXAMPLE 2

Isolation of A83543A and A83543D from fermentation broth

Fermentation broth (185 liters) was added to an equal volume of acetone. The resulting mixture was filtered using a ceramic filter to remove the biomass. The pH of the filtrate was adjusted to pH 13 and then adsorbed onto a 10 liter column of HP-20ss resin (Mitsubishi Chemical Industries Co., Ltd., Japan) and then the A83543A and A83543D components were eluted using a gradient mixture of organic solvent comprising methanol and acetonitrile (1:1)containing 0.1% ammonium acetate. The gradient provile was from 0% organic solvent to 95% organic solvent. Fractions (4 liters) were collected, and based on analytical HPLC, fractions 19 to 26 were combined and concentrated to dryness and then redissolved in 1 liter of methanol for further purification.

I claim:

1. A process for isolating macrolide compounds from a fermentation broth in which they are produced which comprises:

a) providing a fermentation broth which comprises a culture medium capable of meeting the growth requirements of an organism forming a biomass and produce at least one factor having the following formula (a A83543 component);

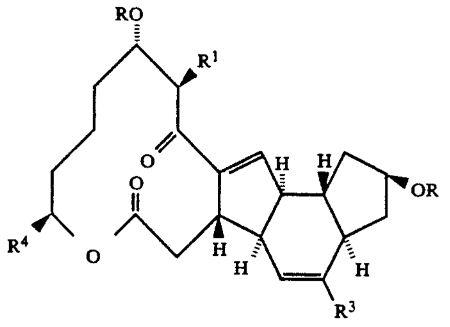

1 wherein

R is H or a group selected from

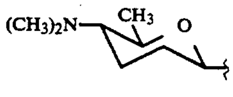

(a)

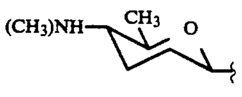

(b)

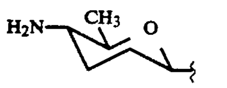

or

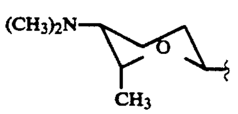

R is

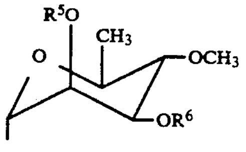

and $R^1$, $R^3$, $R^5$ and $R^6$ are hydrogen or methyl;

$R^4$ is methyl or ethyl; or a phytologically acceptable salt thereof where R is other than hydrogen;

b) adding an approximately equal volume of a water miscible, polar organic solvent to the fermentation broth, including the biomass thereof, under conditions and for a time sufficient to extract the A83543 component from the biomass;

c) separating the liquid phase of the resulting mixture from the biomass;

d) adjusting the pH of the separated liquid phase to between about 7 and 13;

e) applying the separated liquid phase directly to a column of nonfunctional, macroreticular polymer;

f) eluting the A83543 components from the column with a water miscible, polar organic solvent; and g) collecting the fractions containing the A83543 components.

2. The method of claim 1, wherein between steps d and e) the loaded column is washed with a 30% to 70% aqueous solution of water miscible, polar organic solvent to displace the broth from the medium.

3. The process of claim 2 wherein said aqueous solution used to displace the broth from the column is a mixture of methanol, acetonitrile, and water wherein the components are present in a ratio of about 1:1:2.

4. The process of claim 1 wherein the water miscible, polar organic solvent used in step d) is a mixture of up to 95% methanol and acetonitrile wherein the components are present in a ratio of 1:1 and the balance of an aqueous buffer containing 0.1% ammonium acetate.

5. The method of claim 1, wherein the organism is selected from the group of A83543.1 (NRRL No. 18395); A83543.3 (NRRL No. 18537); A83543.4 (NRRL No. 18538); A83543.5 (NRRL No. 18539); A83543.6 (NRRL No. 18719); and A83543.7 (NRRL No. 18720); or mutants thereof.

6. The method of claim 1, wherein the A83543 component is selected from the group consisting of one of the following components

| Factor | $R^3$ | $R^1$ | R | $R^4$ | $R^5$ | $R^6$ |
|---|---|---|---|---|---|---|
| A83543A | H | $CH_3$ | 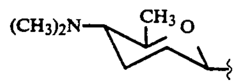 | $C_2H_5$ | $CH_3$ | $CH_3$ |
| A83543B | H | $CH_3$ | 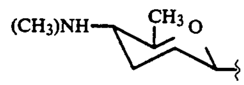 | $C_2H_5$ | $CH_3$ | $CH_3$ |
| A83543C | H | $CH_3$ | 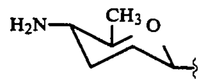 | $C_2H_5$ | $CH_3$ | $CH_3$ |
| A83543D | $CH_3$ | $CH_3$ | 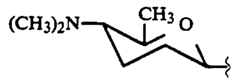 | $C_2H_5$ | $CH_3$ | $CH_3$ |
| A83543E | H | $CH_3$ | 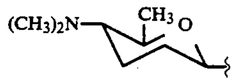 | $CH_3$ | $CH_3$ | $CH_3$ |
| A83543F | H | H | 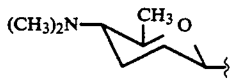 | $C_2H_5$ | $CH_3$ | $CH_3$ |
| A83543G | H | $CH_3$ | 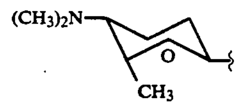 | $C_2H_5$ | $CH_3$ | $CH_3$ |
| A83543H | H | $CH_3$ | 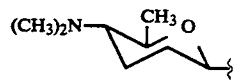 | $C_2H_5$ | H | $CH_3$ |
| A83543J | H | $CH_3$ | 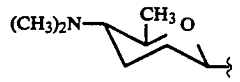 | $C_2H_5$ | $CH_3$ | H |
| A83543L | $CH_3$ | $CH_3$ | 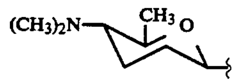 | $C_2H_5$ | $CH_3$ | H |
| A83543M | H | $CH_3$ | 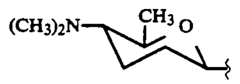 | $C_2H_5$ | $CH_3$ | H |

-continued

| Factor | $R^3$ | $R^1$ | R | $R^4$ | $R^5$ | $R^6$ |
|---|---|---|---|---|---|---|
| A83543N | $CH_3$ | $CH_3$ | 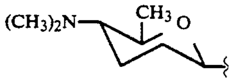 | $C_2H_5$ | $CH_3$ | H |

7. The method of claim 1, wherein the culture medium contains a carbon source selected from the group consisting of glucose, methyl oleate, ribose, xylose, fructose, galactose, mannose, mannitol, maltose, soluble starch, potato dextrin and oils.

8. The method of claim 1, wherein the culture medium contains a nitrogen source selected from the group consisting of cottonseed flour, peptonized milk, corn steep liquor, fish meal, digested soybean meal, yeast extract, enzyme-hydrolyzed casein and beef extract.

9. The method of claim 1, wherein the culture medium contains a nutrient inorganic salt selected from the group consisting of zinc, sodium, magnesium, calcium, ammonium, chloride, carbonate, sulfate and nitrate.

10. The method of claim 1, wherein the fermentation medium contains antifoaming agents.

11. The method of claim 10, wherein the antifoaming agents are selected from the group consisting of soybean oil.

12. The method of claim 1, wherein the liquid phase separating of is separated from the resulting mixture by passing the mixture through a ceramic filter.

13. The method of claim 1, wherein the pH is adjusted between 7 and 10.

14. The method of claim 1, wherein the pH is adjusted using sodium hydroxide.

15. The method of claim 1, wherein the nonfunctional, macroreticular polymer is a nonfunctional, polystyrene crosslinked with divinyl benzene.

16. The method of claim 1, wherein the isolated fractions are concentrated.

17. The method of claim 1, wherein the concentrated fractions are lyophilized.

18. The process of claim 1 wherein the elutant is 95% of the organic solvent containing methanol and acetonitrile wherein the components are present in a ratio of 1:1 and 5% buffer containing 0.1% ammonium acetate.

* * * * *